United States Patent
Ahtchi-Ali et al.

(10) Patent No.: US 7,579,311 B2
(45) Date of Patent: Aug. 25, 2009

(54) NO-STRIP PROCESS FOR PRODUCING BARS COMPRISING ACYL-ISETHIONATE AND FREE FATTY ACID, AND HAVING CONSUMER DESIRABLE PROPERTIES

(75) Inventors: Badreddine Ahtchi-Ali, Newtown, CT (US); Michael Gerard Clarke, Cheshire, CT (US); Florencio Ratuiste, Union, NJ (US); Congling Quan, Milford, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 128 days.

(21) Appl. No.: 11/743,424

(22) Filed: May 2, 2007

(65) Prior Publication Data

US 2008/0272339 A1  Nov. 6, 2008

(51) Int. Cl.
*C07C 143/90* (2006.01)
(52) U.S. Cl. .................... 510/458; 554/92; 260/400
(58) Field of Classification Search .................. 510/458; 554/92
See application file for complete search history.

(56) References Cited

U.S. PATENT DOCUMENTS

| 3,320,292 A | 5/1967 | Cahn et al. |
| 3,376,229 A | 4/1968 | Haass et al. |
| 3,689,437 A * | 9/1972 | McLaughlin ................. 510/158 |
| 4,151,105 A | 4/1979 | O'Roark |
| 4,536,338 A * | 8/1985 | Urban et al. .................. 554/92 |
| 6,069,262 A | 5/2000 | Walele et al. |
| 6,184,399 B1 * | 2/2001 | Zok et al. ..................... 554/92 |
| 2005/0137411 A1 * | 6/2005 | Ahtchi-Ali et al. ............ 554/85 |

FOREIGN PATENT DOCUMENTS

| EP | 0 067 624 A | 12/1982 |
| GB | 2 012 803 A | 8/1979 |
| WO | 2005/063700 A | 7/2005 |

OTHER PUBLICATIONS

International Search Report on International Application No. PCT/EP2008/053676 dated Apr. 7, 2008.

* cited by examiner

*Primary Examiner*—Mark Eashoo
*Assistant Examiner*—M. Reza Asdjodi
(74) *Attorney, Agent, or Firm*—Ronald A. Koatz

(57) ABSTRACT

The present invention relates to process for producing bars comprising 20 to 70% by wt. acyl isethionate and 15% to 35% free fatty acid and which is made by process where excess fatty acids made during production of acyl isethionate is removed by neutralization rather than by "stripping". The bar retains remarkably desirable consumer properties.

7 Claims, 3 Drawing Sheets

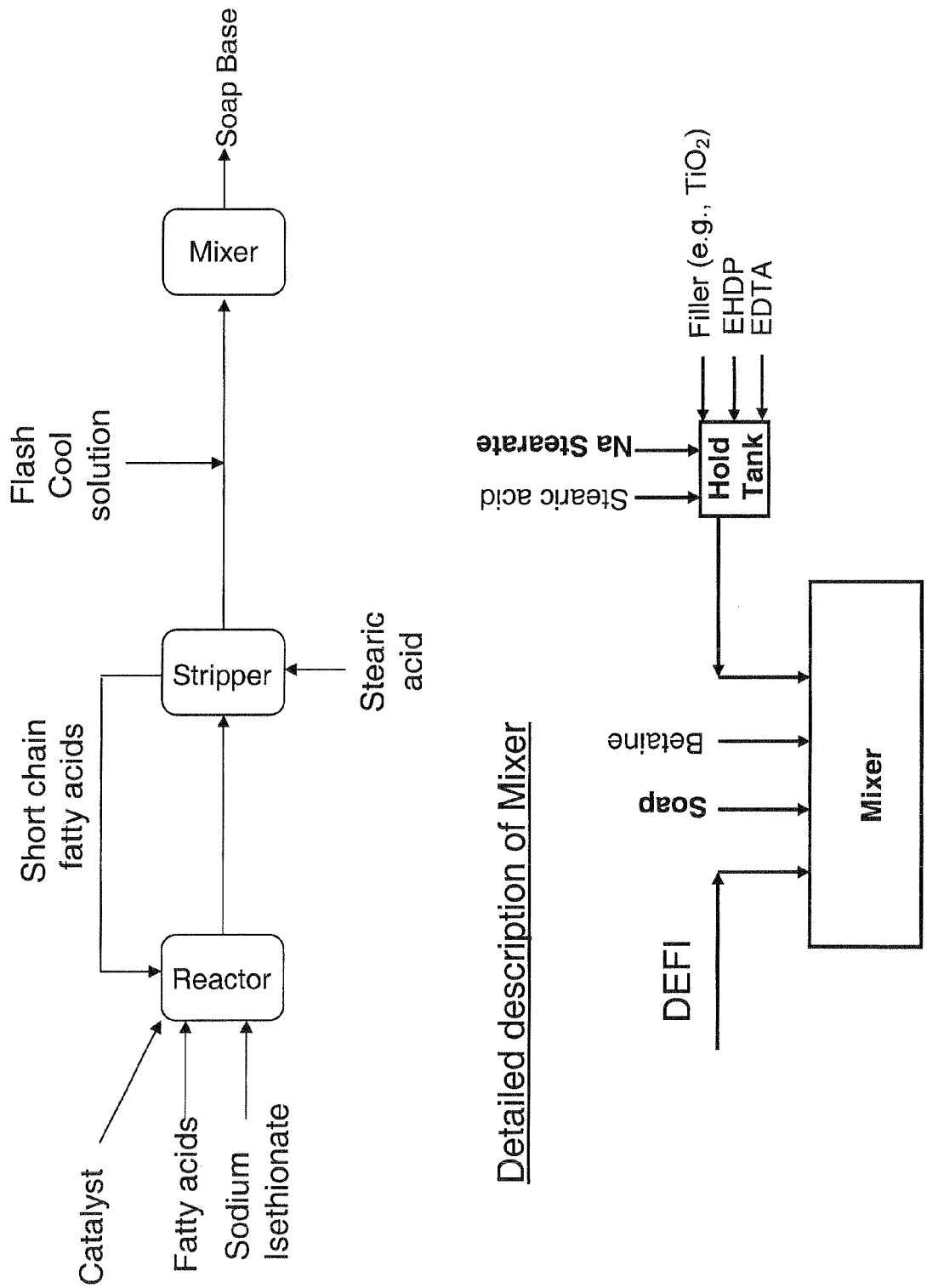

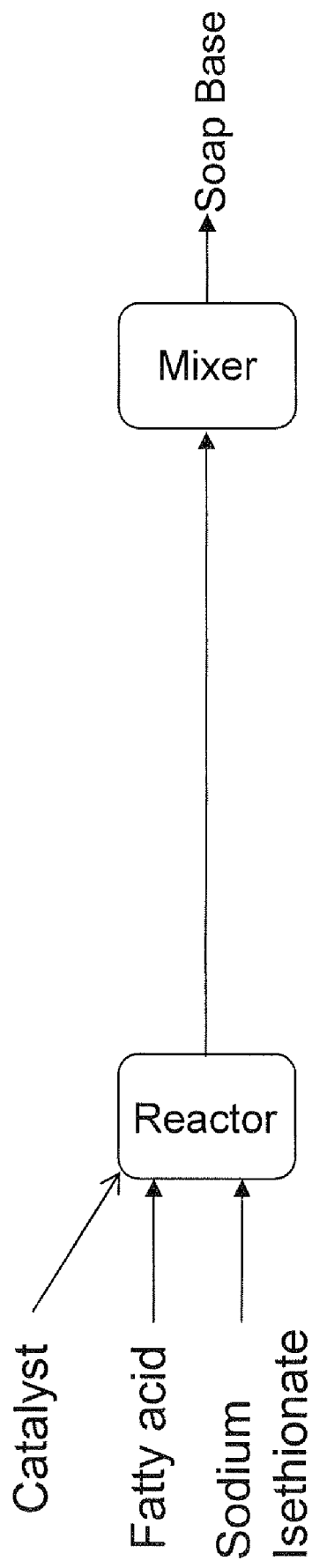
Figure 2. No strip DEFI Process without in-situ soap formation

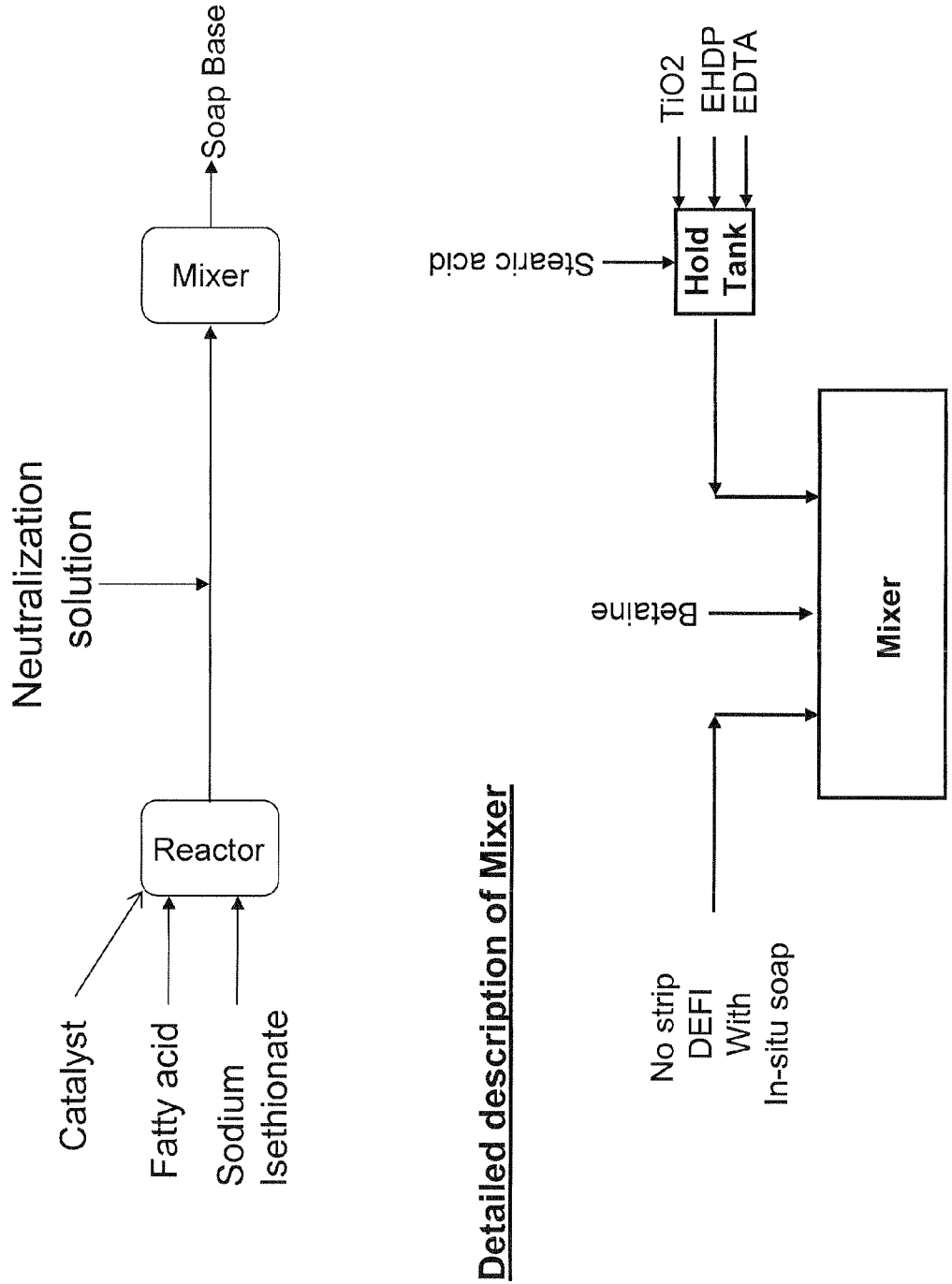

NO-STRIP PROCESS FOR PRODUCING BARS COMPRISING ACYL-ISETHIONATE AND FREE FATTY ACID, AND HAVING CONSUMER DESIRABLE PROPERTIES

FIELD OF THE INVENTION

The present invention relates generally to production of soap bars in which the bar is predominantly alkali metal or ammonium alkanoyl isethionate (e.g., sodium lauroyl or sodium cocoyl isethionate), and which also contain at least about 15%, preferably at least 20% by weight free fatty acid (typically derived during production of the alkanoyl isethionate). More particularly, it relates to a process for making alkanoyl isethionate in a way that the conversion rate (from fatty acids and alkali metal or ammonium isethionate reactants used to make it) to alkanoyl isethionate is sufficiently high without causing processing issues (e.g., greater than 60% conversion, preferably greater than 70% conversion, without attendant processing issues), while simultaneously ensuring that the resultant mix of fatty acid, and the reaction conditions produce a final bar which lathers well (e.g., greater than 80 ml measured by defined test) and is not too gritty (e.g., no more than 10 grit/sand particles measured by defined test). The process is a non-strip process whereby excess fatty acids resulting from the conversion reaction are directly neutralized (rather than being "stripped" as in previous processes) in a flash cooling reaction to minimize the extent of lather suppressing fatty acids, while providing the simultaneous benefit of providing soap in situ (which soap is found in the final base bar compositions anyway).

BACKGROUND

The present invention relates to the production of soap bar bases, particularly those comprising alkali metal or ammonium alkanoyl isethionate in the final bar.

Typically, the production of the alkanoyl isethionate used in the bars results from the reaction of (1) fatty acids (typically predominantly $C_{12}$-$C_{14}$ fatty acids such as coconut oils or palm kernel acids which are used in the reaction) and (2) alkali metal or ammonium isethionate (e.g., sodium isethionate, $HOCH_2CH_2SO_3N_a$).

The direct esterification of fatty acid and isethionate results in the production, depending on the rate of conversion, of directly esterified fatty acyl isethionate (DEFI). In a typical DEFI reaction, for example, coconut fatty acid may be reacted with sodium isethionate (e.g., at ratio of greater than 1:1) and reaction mixture are then pumped to a "stripper" reactor. In the stripper reactor, typically some of the shorter chain fatty acids are "stripped" (and recycled to the first reactor), while some longer chain fatty acids (e.g., $C_{16}$-$C_{20}$ fatty acids such as, for example, stearic acid) are added. While not wishing to be bound by theory, it is believed that the longer chain fatty acids help both to ensure there is a proper ratio of long to short chain fatty acids in the final bar such that acceptable lather values are obtained (e.g., at least 80 ml lather volume), as well as to minimize regions of sodium stearate formation which can account for grittiness.

Although the resultant DEFI solution (i.e., solution comprising converted DEFI and unconverted fatty acids and isethionates) produced in a typical "stripper" reaction is adequate, it would be a substantial benefit to eliminate the "stripper" step because it would result in an entire process step which would not be required. The savings in equipment costs and maintenance, space savings etc. would result in tremendous efficiencies and potentially millions of dollars worth of savings. Thus, applicants have long considered it a desirable goal to find a way to so eliminate the strip step in a so-called "no-strip" process.

There thus seems to be a need to find a way to remove excess free fatty acid (e.g., previously done by a "stripper" process) since providing a larger excess of fatty acid leads to softer, difficult to process bars.

Unexpectedly, applicants have found that, when the reactants are combined as has been previously done to provide DEFI solution (resulting in DEFI, and unreacted fatty acids and isethionate), if, rather than strip away the typically shorter chain fatty acids and add longer chain fatty acid at the stripping stage, the hot DEFI solution is quenched and neutralized (e.g., by addition of sodium hydroxide solution), and the fatty acids are converted to soap in situ. This neutralization both reduces the level of foam-suppressing fatty acid (more soap, less fatty acid), and further allows the soap to be used with the bar base rather than have to add soap in a different step.

BRIEF DESCRIPTION OF THE INVENTION

More specifically, the invention comprises a no-strip process for producing a bar base having:
(1) 20 to 70%, preferably 25 to 65% by wt. final bar composition of acyl isethionate of final product without free fatty acid in it and
(2) 15 to 35% by wt. final bar of free fatty acid, said final bar having lather of at least 80 ml, preferably at least 85, more preferably at least 100, more preferably at least 110 ml of lather volume as measured by the Bar Lather Appraisal Method outlined in the Protocol section; and a grit/sand value of no more than 10 particles, preferably 8 or less, more preferably 6 or less, even more preferably 5 or less, even more preferably 4 or less and even more preferably 3 or less (most preferably 1 or absent) at 35° C. or lower as measured by the Bar Wash Down Procedures summarized in the protocol section, wherein said process comprises
(1) reacting (a) fatty acid $RCO_2H$ and (b) isethionate $HOR'SO_3M$ to produce (a) directly esterified fatty acid $RCO_2R'SO_3M$ plus (b) $H_2O$ plus (c) unreacted fatty acids and isethionate;
wherein M is alkali metal or ammonium ion and/or is $C_{12}$ to $C_{24}$ monovalent aliphatic hydrocarbon, R is $C_5$ to $C_{24}$ straight chain or unsaturated alkyl and R' is divalent, aliphatic hydrocarbon having 2 to 4 carbons;
wherein the conversion rate to acyl isethionate is greater than about 60% e.g., 60-90%;
(2) adding solution of a neutralizing agent selected from the group consisting of metal hydroxide, metal oxides, metal salts and mixtures thereof (preferably the metal hydroxide, oxide or salt is an alkali metal hydroxide, oxide or salt) to neutralize unreacted fatty acid and form in-situ soap;
(3) transferring acyl isethionate solution comprising the acyl isethionate, fatty acid, in-situ soap and isethionate to a container holding ingredients which will be in final bar composition (in addition to what is in isethionate solution); and
(4) cooling reactants to form bar chips.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

BRIEF DESCRIPTION OF THE DRAWINGS

FIG. 1 is figure showing schematic of process used where fatty acid and isethionate are combined and stripped (typically to remove shorter chain fatty acids).

FIG. 2 is schematic of process without stripper when longer chain fatty acids and shorter chain fatty acids are mixed in same reactor.

FIG. 3 is a schematic of flash cool neutralization (e.g., with sodium hydroxide) of no-strip DEFI before adding other ingredients in mixture. The neutralization leads to reduced fatty acid in DEFI solution going to mixer.

DETAILED DESCRIPTION OF THE INVENTION

The present invention relates to a novel no-strip process used in the production of base bar chips ("chips" are formed when ingredients comprising the final bar are mixed and cooled; the chips are typically extruded into "logs" before being cut and stamped into final bars as is well know in the art), particular bar chips comprising 20 to 70% by wt., preferably 25 to 65% by wt. of final bar acyl isethionate and 15-35% final bar free fatty acid.

Typically, such bar base materials are formed by first reacting components to make DEFI (a product made from fatty acids and isethionate to form acyl isethionate; the acyl isethionate contains some portion of unreacted fatty acids), and combining DEFI with other base bar materials to form the base chips.

DEFI itself is typically formed by reacting shorter chain fatty acids and isethionate in the reactor. The product is then pumped to a stripper where some of the shorter chain acids are removed, and longer chain fatty acids are added creating the right blend which will be found in the final base bar (see FIG. 1).

According to the subject invention, the stripping process can be avoided altogether (resulting in huge cost savings). A novel flash-cool neutralization process where a neutralizing solution converts excess fatty acids to soap in situ is used in place of the stripping process (see FIG. 3). This novel process results in bars with good lather, good processibility, and no grit. The process is described in greater detail below.

Preparation of DEFI

The first step in the process of preparing the base bar chips is production of directly esterified fatty acyl isethionate (DEFI) from fatty acids and alkali metal or ammonium isethionate.

The process is shown below:

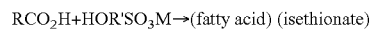
$RCO_2H + HOR'SO_3M \rightarrow$ (fatty acid) (isethionate)

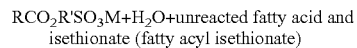
$RCO_2R'SO_3M + H_2O$ + unreacted fatty acid and isethionate (fatty acyl isethionate)

Where M is alkali metal (e.g., sodium, potassium, lithium, particularly sodium is preferred) or ammonium ion, R is monovalent aliphatic hydrocarbon having 7 to 24, preferably 8 to 22 carbon atoms; and R' comprises divalent aliphatic hydrocarbon atoms having 2 to 4 carbons.

Typically, the reaction occurs by heating ingredients to temperature of 190-255° C. in the presence of a catalyst (e.g., zinc oxide, zinc soap, mixtures of zinc oxide and organic sulfonic acid; group 4 metal catalysts). Typically, the molar ratio of fatty acid to isethionate is between about 1:1 to 2:1.

Typically, the DEFI reaction will use fatty acids wherein chain length of fatty acid is preferably, $C_6$-$C_{20}$. Because of processing issues (e.g., related to excess fatty acids), it is typically difficult to obtain good conversion rates unless the excess fatty acids are removed in a "stripper" reaction.

According to the process of the subject invention, the excess fatty acids are removed instead via neutralization.

Thus, the present invention provides a process where there is a conversion rate to acyl isethionate of greater than about 60% (preferably 60 to 90% conversion) even when stripping step is not used.

Thus, according to the first step of the present process, preferably predominantly short chain fatty acids ($C_6$-$C_{20}$) are reacted as noted with isethionate to provide a DEFI solution comprising the DEFI and excess fatty acid and isethionate.

As indicated, in the absence of a stripping step, the excess fatty acid from the reaction step is detrimental to bar processibility and properties.

Neutralization Step

According to the second step of the subject invention, a sufficient amount of neutralizing solution (e.g., metal hydroxide, especially alkali metal hydroxides; metal oxides; metal salts; or mixtures thereof) is added to reduce the level of unreacted fatty acid in the DEFI solution coming out of the reactor. This reduction is caused by the formation of soap, in situ, from the increased free fatty acid.

Typically, about 10-90% of the free acid is neutralized. Typically, the DEFI solution coming out of the DEFI reactor is a molten solution. When formed, the molten DEFI typically has a temperature of about 220-240° C. The neutralizing solution is typically added to the molten DEFI at room temperature, e.g., about 25° C. Because the molten DEFI has a very high temperature, i.e., around 220 to 240° C., it has to be cooled before it will be mixed with the other ingredients of the product in the mixer. Cooling the DEFI is achieved by flash cooling wherein the neutralizing solution, e.g., 18% to 50% of caustic, is injected to the DEFI stream just prior to the main mixer.

One advantage of the neutralization step is that, rather than having to add additional soap into the mixer, soap can be formed from the neutralization of fatty acid.

After neutralizing, the neutralized DEFI solution is transferred (e.g., by pumping) to a mixer where additional ingredients are charged to form the basis of the final chip (see FIG. 3).

In addition to surfactants (e.g., betaine, ether sulfate), perfumes, preservation agents (e.g., EHDP, EDTA), fillers ($TiO_2$), etc. which may be added which are different to what is already in the DEFI solution, compounds which are already present in the solution (e.g., soap, isethionate) may also be added. EHDP is Ethane-1-hydroxy-1,1diphosphonate. EDTA is ethylenediaminetetraacetic acid.

Typically, the mixing reaction occurs at temperature of from about 100 to 130° C. and the reactants are mixed from about 15 to 90 minutes.

The reactants are then cooled to form chips which are the subject of the invention. The chips, alone or in combination with other chips, may then be passed through an extruder and formed into logs, cut and stamped into final bars.

Typically, bars of the invention made according to the no-strip, neutralization process of the invention will have grit particle value (as defined below) of below 7, preferably below 5 and more preferably below 3. In addition, the bar will have lather value above 110, preferably above 120, more preferably above 125 ml.

Protocols

Bar Lather Appraisal Method (BLAM)—Funnel Method

Principle

To determine the volume of lather which can be generated and collected from a given bar formulation under a strict regiment of washing.

Apparatus

Toilet bars 2 large sinks

Surgical gloves

Measuring funnel

The measuring funnel is constructed by fitting a 10 ½ inch diameter plastic funnel to a graduated cylinder which has had the bottom cleanly removed. Minimally the graduated cylinder should be 100 cc's. The fit between the funnel and the graduated cylinder should be snug and secure.

Procedure

Note: The bar to be evaluated must first be conditioned to remove the superficial layer. This is done by turning the bar under running water 20 to 25 times. Lay the bar aside, and then repeat one more time. The bar is now ready for evaluation.

Before evaluations proceed, place the measuring funnel into one of the sinks and fill the sink with water until the 0 cc mark is reached on the graduated cylinder.

i. Run the faucet in the second sink and set the temperature to 95° F. (35° C.).
ii. Holding the bar between both hands under running water, rotate the bar for ten (10) half turns.
iii. Remove hands and bar from under the running water.
iv. Rotate the bar fifteen (15) half turns.
v. Lay the bar aside.
vi. Work up lather for ten (10) seconds.
vii. Place funnel over hands.
viii. Lower hands and funnel into the first sink.
ix. Once hands are fully immersed, slide out from under funnel.
x. Lower the funnel to the bottom of the sink.
xi. Read the lather volume.
xii. Remove the funnel with lather from the first sink and rinse in the second sink.

The test should be performed on 2 bars of the same formulation, same batch etc. and the volume should be reported as an average of the 2 assessments.

Note: During lather generation a subjective measurement of the bar and lather quality may be made (e.g. slip, drag, creaminess, bubble size etc.)

Bar Wash Down Procedures

Principle

The finished bar is washed down in tap water adjusted to 23° C. to 25° C. The surface texture of the washed bar is then graded as "nil", "smooth", "slightly gritty/sandy", "moderately gritty/sandy", or "considerably gritty/sandy".

Procedure

Adjust the temperature of the running tap water to 23° C.-25° C. temperature by mixing hot and cold tap water. Hold the bar in the stream of running tap water and wash it down for one minute by revolving it gently by rubbing it in the hands. At the end of this period, note the surface texture of the wet bar. If hard particle grit/sand is felt, count the actual number of particles, and referring to the rating scale below, report the bar as "nil", "smooth", "slightly gritty/sandy", "moderately gritty/sandy", or "considerably gritty/sandy". If pumice type sand is noted, estimate the area of bar containing the pumice, and again referring to the rating scale, report the texture of the bar.

If any bar is rated "moderately gritty/sandy" or "considerably gritty/sandy", it may be washed down again for one minute under running tap water adjusted to 28° C.-30° C. temperature by rubbing and revolving the bar as above. At the end of this period, again note the texture of the wet bar, and using the rating scale, report the texture of the bar.

When reporting the texture of a bar, always include the temperature of the water used.

| SAND/GRIT PARTICLES Number of Particles | PUMICE SAND Area of Face | RATING |
|---|---|---|
| 0 | <⅛ of one face | Nil |
| 1-2 | Very small amount | Smooth |
| 3-4 | ¼ of one face | Slight |
| 5-6 | ¼-½ of one face | Moderate |
| >7 | >½ of one face | Considerable |

EXAMPLES

Example 1 and Control Examples A & B

| Example | Description: | Grit Value After Wash Down | Lather, ml |
|---|---|---|---|
| Control A | With No-strip DEFI, not neutralized | >7 at 25 C., 6 at 35 C. | 107 |
| Control B | With stripped DEFI | 0 at 25 C. | 142 |
| Example 1 | With No-strip DEFI, neutralized | 0 at 25 C. | 120 |

According to Example 1 and Control Examples A and B, applicants first formed DEFI in a reactor combining sodium isethionate and fatty acids at temperature of about 220° to 240° C. to form the DEFI. In control A example, excess fatty acids were not "stripped" (removed), but no neutralization (e.g., addition of alkali metal hydroxide) was done. In Control B, the excess fatty acid was removed in a stripper reaction. In Example 1, as per the invention, neutralization with sodium hydroxide was used instead of stripping.

The DEFI, whether stripped or not, was flash cooled (using neutralizing agent in Example 1 and not using neutralizing agent in Controls A and B) and combined in a mixer with betaine, sodium stearate and minors (e.g., fillers, preservatives) at temperature between 100 and 130° C. The mix was cooled, extruded into logs, cut and stamped into bars. These are the bars used for grit test, and testing was done according to noted protocol.

As seen, when no-strip and no neutralization is used (Control A), relatively high grit is seen. By contrast, when neutralization is used (Example 1), grit values are comparable to the typical reaction in which stripping is used (Control B).

Example 2 and 3 and Control Examples C & D

| Example | Description | Wash Down | Lather, ml |
|---|---|---|---|
| Example 2 | With No-strip DEFI, neutralized | 0 at 25 C. | 139 |
| Control C | With No-strip DEFI, not neutralized | 0 at 25 C. | 111 |
| Example 3 | With No-strip DEFI, neutralized | 0 at 25 C. | 140 |
| Control D | With stripped DEFI | 0 at 25 C. | 140 |

Bars 2 and 3 and Control C & D were prepared as in Examples 1 and Control A & B above.

This example shows that when no-strip method was used, followed by neutralization (Example 2 and 3), lather scores were comparable to those when fatty acid stripping (Control D) was used.

The invention claimed is:

1. A no-strip process for producing a bar base having about 20-70% by wt. final bar acyl isethionate and about 15-35% by wt. free fatty acid and wherein the bar has lather of at least 80 ml lather volume as measured by the Bar Lather Appraisal Method and bar has grit of no more than 10 grit particle at 35° C. as measured by Bar wash Down Procedures, wherein said process comprises:

(1) producing a directly esterified fatty acid isethionate (DEFI) by reacting fatty acid with alkali metal isethionate or ammonium isethionates in a reactor according to reaction shown:

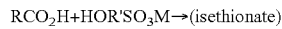

$RCO_2H + HOR'SO_3M \rightarrow$ (isethionate)

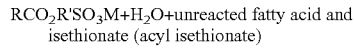

$RCO_2R'SO_3M + H_2O$ + unreacted fatty acid and isethionate (acyl isethionate)

wherein M is alkali metal or ammonium ion;

R is $C_5$-$C_{24}$ straight chain or unsaturated alkyl group and R' is divalent, aliphatic hydrocarbon atoms having 2 to 4 carbons, wherein conversion rate to acyl isethionate is > about 60%;

wherein the DEFI coming out of the reactor is a molten DEFI solution having a temperature about 220° to 240° C.;

(2) adding solution of a neutralizing agent to said molten DEFI solution at a temperature of about 25° C., said agent being selected from the group consisting of metal hydroxides, metal oxides and mixtures thereof in an amount sufficient to neutralize 10 to 90% of unreacted fatty acid and form in-situ soap, $RCO_2M$;

wherein said solution of neutralizing agent both reacts with unreacted fatty acid to form soap as noted and cools reaction to temperature of about 100 to 150° C. where DEFI can be mixed with other ingredients prior to transferring to such mixer;

(3) transferring acyl isethionate solution (comprising acyl isethionate, fatty acid, in-situ soap and metal isethionate) to container holding one or more ingredients which will be in base bar composition besides what is in acyl isethionate solution;

(4) cooling reactants of (3) to form base bar chips.

2. A process according to claim 1, wherein the neutralizing solution is added without having previously removed or stripped unreacted free fatty acid from the acyl isethionate reaction solution following reaction.

3. A process according to claim 1 comprising 25 to 65% by wt. final bar acyl isethionate.

4. A process according to claim 1, wherein bar has lather of at least 85 ml.

5. A process according to claim 4, wherein bar has lather of at least 100 ml.

6. A process according to claim 1, wherein bar has grit of 8 or less grit particle at 35° C.

7. A process according to claim 1, wherein neutralizing solution comprises alkali metal hydroxide.

* * * * *